US00PP33004P2

(12) United States Plant Patent
Smith

(10) Patent No.: US PP33,004 P2
(45) Date of Patent: Apr. 27, 2021

(54) ***CHRYSANTHEMUM* PLANT NAMED 'CIFZ0077'**

(50) Latin Name: ***Chrysanthemum* x *morifolium***
Varietal Denomination: CIFZ0077

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/898,540

(22) Filed: Jun. 11, 2020

(51) Int. Cl.
*A01H 6/14* (2018.01)
*A01H 5/02* (2018.01)

(52) U.S. Cl.
USPC ..... Plt./290
CPC ..... *A01H 6/1424* (2018.05); *A01H 5/02* (2013.01)

(58) Field of Classification Search
USPC ..... Plt./290
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0077' particularly distinguished by its medium size plant with round mound plant habit, a medium to large size decorative flower (2.0 inch), bronze flower color and a natural season response late September.

1 Drawing Sheet

Latin name of the genus and species of the plant claimed: *Chrysanthemum* x *morifolium*.

Varietal denomination: 'CIFZ0077'.

BACKGROUND OF THE NEW PLANT

The present invention comprises a new *Chrysanthemum*, botanically known as *Chrysanthemum* x *morifolium*, and hereinafter referred to by the variety name 'CIFZ0077'.

'CIFZ0077' is a product of a planned breeding program. The new cultivar has a medium size plant with round mound plant habit, a medium to large size decorative flower (2.0 inch), bronze flower color and a natural season response late September.

'CIFZ0077' originated from a mutation of X-ray treated cuttings in October 2014 in Gilroy, Calif. 'CIFZ0077' was selected from the resulting plants on Mar. 3, 2015 in Gilroy, Calif.

The female parent was the variety 'Yowanda', U.S. Plant Pat. No. 20,210.

TABLE 1

A COMPARISON BETWEEN THE FEMALE PARENT AND 'CIFZ0077':

| Trait | CIFZ0077 | 'Yowanda' |
|---|---|---|
| Natural response: | Couple days faster | Couple days slower |
| Blackcloth response: | Similar | Similar |
| Flower size: | Similar | Similar |
| Flower color: | Bronze | Lavender |
| Flower type: | Similar | Similar |
| Plant size: | Similar | Similar |
| Plant habit: | Similar | Similar |
| Plant strength: | Softer | Sturdier |

As the new variety is the result of mutation breeding, there is not a male parent.

The first act of asexual reproduction of 'CIFZ0077' was accomplished when vegetative cuttings were propagated from the initial selection in April 2015 in Gilroy, Calif.

BRIEF SUMMARY OF INVENTION

Horticultural examination of plants grown from cuttings of the plant initiated in April 2015 and continuing thereafter, has demonstrated that the combination of characteristics as herein disclosed for 'CIFZ0077' are firmly fixed and are retained through successive generations of asexual reproduction.

'CIFZ0077' has not been observed under all possible environmental conditions. The phenotype may vary significantly with variations in environment such as temperature, light intensity and day length.

A Plant Breeder's Right for this cultivar has not yet been applied for. 'CIFZ0077' has not been made publicly available prior to the effective filing date of this application, notwithstanding any disclosure that may have been made less than one year prior to the effective filing date of this application by the inventor or another who obtained 'CIFZ0077' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0077' with colors being as true as possible with an illustration of this type.

Figure 1:
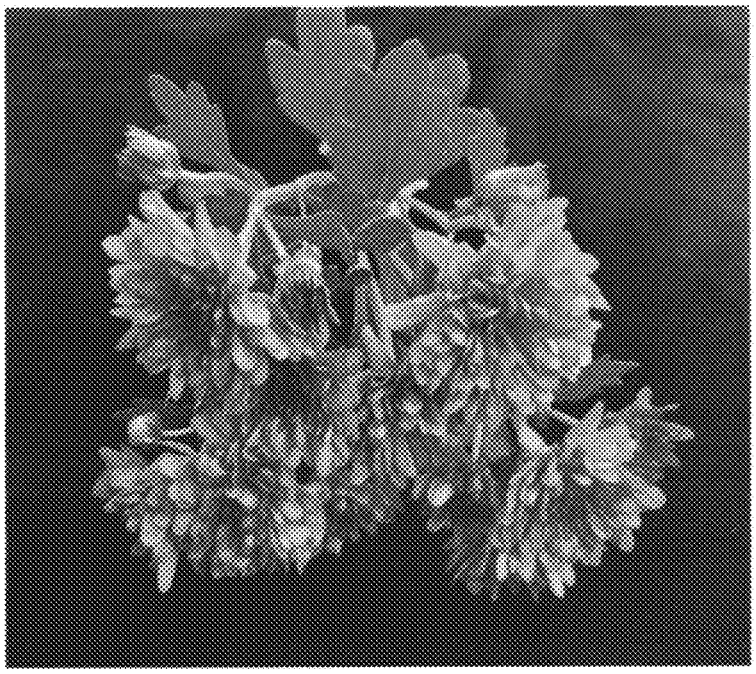
Figure 2:
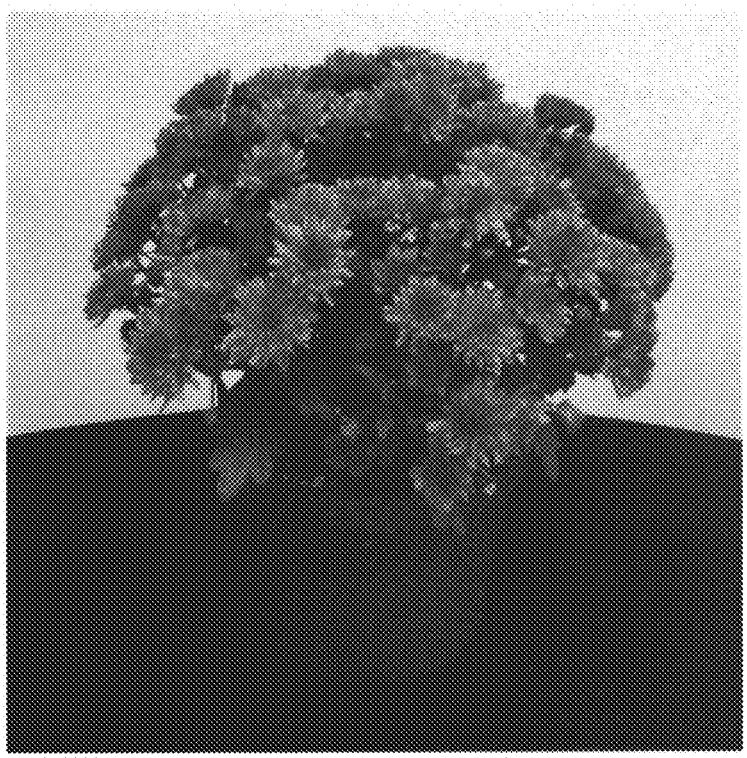

The photographic drawings show in FIG. 1 a close view of flower of the new variety and in FIG. 2 a flowering plant from an outdoor trial.

The aforementioned photographs: FIG. 1, as well as FIG. 2, were taken in September 2019 both showing a plant from the same blackcloth indoor trial in Gilroy, Calif. These plants were about 10 weeks of age. One rooted cutting per pot had been planted in a one gallon pot, not pinched in week 24, and black clothed from week 25. Plants started flowering the end of August.

DETAILED BOTANICAL DESCRIPTION

The measurements were taken in Gilroy, Calif., in September 2019 on the plants from the aforementioned trial.

Color references are made to The Royal Horticultural Society Colour Chart (R.H.S.) 2015.

TABLE 2

DIFFERENCES BETWEEN THE NEW VARIETY 'CIFZ0077' AND TWO MOST SIMILAR VARIETIES:

| Trait | 'CIFZ0077' | 'Yomiranda', U.S. Plant Pat. No. 16,848 |
|---|---|---|
| Natural response: | ¾ week slower | ¾ week faster |
| Blackcloth response: | Similar | Similar |
| Flower size: | Similar | Similar |
| Flower color: | Similar | Similar |
| Flower type: | Similar | Similar |
| Plant size: | Larger | Smaller |
| Plant habit: | More domed | More flat topped |

TABLE 3

| Trait | 'CIFZ0077' | 'Conella Orange', Not patented |
|---|---|---|
| Natural response: | Similar | Similar |
| Blackcloth response: | Couple days faster | Couple days slower |
| Flower size: | Larger | Smaller |
| Flower color: | Darker/less yellowy | Lighter/more yellowy |
| Flower type: | Similar | Similar |
| Plant size: | Larger | Smaller |
| Plant habit: | Similar | Similar |
| Flowering uniformity: | Less uniform | More uniform |

Plant:

*Form, growth and habit.*—Herbaceous garden-type, stems Upright and outwardly spreading, freely branching, strong and moderately vigorous growth habit.

*Plant height (above soil).*—17-20 cm.

*Plant height (inflorescence included).*—21-23 cm.

*Plant width.*—33-35 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 147A.

*Immature leaf, color lower surface.*—RHS 139A.

*Mature leaf, color, upper surface.*—RHS 139A.

*Mature leaf, color lower surface.*—RHS 137B.

*Length.*—5.2 cm.

*Width.*—3.8 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Few.

*Depth of margin indentations.*—Shallow.

*Leaf length terminal lobe relative to total leaf length.*—Terminal lobe is ¼ to ⅓ the length of the total leaf=Short.

*Leaf depth lower lateral sinus.*—Shallow.

*Texture, upper surface.*—Bifid hairs.

*Texture, lower surface.*—Bifid hairs.

*Color of veins, upper surface.*—RHS 145A.

*Color of veins, lower surface.*—RHS 145B.

*Pattern of veining.*—Palmate.

*Petiole color.*—RHS 137A.

*Petiole length.*—1.4 cm.

*Diameter.*—0.3 cm.

*Texture.*—Bifid hairs.

*Presence of stipules.*—Not present.

Stem:

*Quantity of main branches per plant.*—8-10.

*Color of stem.*—RHS 143C.

*Length of stem.*—8.0-9.0 cm.

*Diameter.*—0.4 cm.

*Length of internodes.*—0.5-4.0 cm.

*Texture.*—Bifid hairs.

*Color of peduncle.*—RHS 143A.

*Length of peduncle.*—2.5-3.5 cm.

*Peduncle diameter.*—0.2 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 6 weeks.

*Natural season flowering.*—Late September.

*Quantity of inflorescences per plant.*—90-120 with many small buds developing.

*Lastingness of individual blooms on the plant.*—About five weeks from first color.

*Fragrance.*—Slightly spicy.

Bud (when showing color):

*Color.*—RHS 53B, with white overtone.

*Length.*—1.5 cm.

*Width.*—1.0 cm.

*Shape.*—Oblate.

Immature inflorescence (at moment of opening):

*Diameter.*—3.0 cm.

*Color of ray florets, upper surface.*—RHS 23A in center, with a faint of RHS N34A around the tips.

*Color of ray florets, lower surface.*—RHS 16A in center, with a faint of RHS N34A around the tips.

Mature inflorescence:

*Diameter.*—4.5 cm.

*Depth.*—1.5 cm.

*Total diameter of disc.*—0.3 cm to no disc present.

*Receptacle color.*—RHS 16A.

*Receptacle height.*—0.4 cm.

*Receptacle diameter.*—0.5 cm.

*Length of corolla tube.*—Medium.

Ray florets:

*Average quantity of florets.*—140-160 in several whorls.

*Color of florets, upper surface (abaxial).*—Outer layers RHS 23A with RHS N34A faintly around the tips.

*Color inner surface* (*adaxial*).—RHS 16A with RHS N34A faintly around the tips.
*Length.*—1.5 cm.
*Width/diameter.*—0.5 cm.
*Shape.*—Elliptical.
*Apex shape.*—Mostly obtuse and dentate.
*Base shape.*—Tube.
*Margin.*—Entire. Small incisions may be present at tip.
*Margin.*—Type of rolling: Flat.
*Texture, upper surface.*—Papillate.
*Lower surface.*—Papillate.
*Ribs present.*—Yes.
*Number of keels.*—0.

Disc florets:
*Number of disc florets.*—Up to 200, may not be present in all flowers.
*Width.*—Up to 0.5 cm.
*Length.*—3.0 cm.
*Color.*—RHS 16A; RHS 144B at base.

Inflorescence (at moment of senescence):
*Color of ray florets, upper surface.*—Outer layers RHS 21B, with RHS 34C around the tips.
*Color of ray florets, lower surface.*—RHS 16A with RHS N34A faintly around the tips.

Phyllaries:
*Quantity.*—22.
*Color, upper surface.*—RHS 143C.
*Color, lower surface.*—RHS 143A.
*Length.*—0.5 cm.
*Width.*—0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.5 cm.
*Style color.*—RHS 150C.
*Style length.*—0.4 cm.
*Stigma color.*—RHS 7D.
*Stigma shape.*—Bi-parted.
*Ovary color.*—RHS 145C.
*Ovary length.*—0.2 cm.
*Ovary width.*—0.1 cm.

Androecium:
*Stamens.*—1, found on only disc florets.
*Color of filaments.*—RHS 2B.
*Length filaments.*—0.2 cm.
*Anther color.*—RHS 13A.
*Anther length.*—0.2 cm.
*Anther shape.*—Oval to club shaped.
*Color of pollen.*—RHS 13A.
*Pollen amount.*—Moderate.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0077' substantially as illustrated and described herein.

* * * * *